(12) United States Patent
Miletic et al.

(10) Patent No.: US 8,679,480 B2
(45) Date of Patent: Mar. 25, 2014

(54) METHOD TO INHIBIT NEUROPATHIC PAIN BY INTRATHECAL INJECTION OF PROTEIN PHOSPHATASES

(75) Inventors: Vjekoslav Miletic, Cross Plains, WI (US); Gordana Miletic, Cross Plains, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/524,115

(22) Filed: Jun. 15, 2012

(65) Prior Publication Data

US 2012/0321610 A1 Dec. 20, 2012

Related U.S. Application Data

(60) Provisional application No. 61/498,796, filed on Jun. 20, 2011.

(51) Int. Cl.
*A61K 38/43* (2006.01)

(52) U.S. Cl.
USPC .......................... 424/94.6; 435/197; 514/21.2

(58) Field of Classification Search
USPC ................ 424/94.6, 94.1; 435/197, 196, 195; 514/21.2
See application file for complete search history.

(56) References Cited

U.S. PATENT DOCUMENTS 7,026,118 B1  4/2006 Wei et al.
2004/0120940 A1* 6/2004 Kiss .............................. 424/94.6

OTHER PUBLICATIONS

Luan "Protein Phosphatases in Plants" (2003) Annual Review of Plant Biology, vol. 54: 63-92.*
Abel T, Kandel E (1998), Positive and negative regulatory mechanisms that mediate long-term memory storage. *Brain Res Rev* 26:360-378.
Baumgartel K, Genoux D, Welzl H, Tweedie-Cullen RY, Koshibu K, Livingstone-Zatchej M, Mamie C, Mansuy IM (2008), Control of the establishment of aversive memory by calcineurin and Zif268. *Nature Neurosci* 11:572-578.
Bennett GT, Xie YK (1997), A peripheral mononeuropathy in rat that produces disorders of pain sensation like those seen in man. *Pain* 33:87-107.
Citri A, Malenka RC (2008), Synaptic plasticity: multiple forms, functions, and mechanisms. *Neuropsychopharmacol* 33:18-41.
Dworkin et al., Recommendations for the Pharmacological Management of Neuropathic Pain: An Overview and Literature Update, *Mayo Clin Proc.*, Mar. 2010;85(3)(suppl):S3-S-14.
Goto S, Hirano A, Pearson T (1990), Calcineurin and synaptophysin in the human spinal cord of normal individuals and patients with familial dysautonomia. Acta *Neuropathol* 79:647-652.
Groth RD, Dunbar RL, Mermelstein PG (2004), Calcineurin regulation of neuronal plasticity. *Biochem Biophys Res Comm* 311:1159-1171.
Groth RD, Coicou LG, Mermelstein PG, Seybold VS (2007), Neurotrophin activation of NFAT-dependent transcription contributes to the regulation of pro-nociceptive genes. *J Neurochem* 102:1162-1174.
Ji RR, Strichartz, G (2004), Cell signaling and the genesis of neuropathic pain. *Science's STKE* 252:re14.
Latremoliere A, Woolf CT (2009), Central sensitization: a generator of pain hypersensitivity by central neural plasticity. *J Pain* 10:895-926.
Lee, HK (2006), Synaptic plasticity and phosphorylation. *Pharmacol Therap* 112: 810-832.
Masumura C, Horii A, Mitani K, Kitahara T, Uno A, Kubo T (2007), Unilateral vestibular deafferentation-induced changes in calcium signaling-related molecules in the rat vestibular nuclear complex. *Brain Res* 1138:129-135.
Miletic G, Pankratz MT, Miletic V (2002), Increases in the phosphorylation of cyclic AMP response element binding protein (CREB) and decreases in the content of calcineurin accompany neuropathic pain following chronic constriction injury in rats. *Pain* 99:493-500.
Miletic G, Miletic V (2008), Loose ligation of the sciatic nerve is associated with TrkB receptor-dependent decreases in KCC2 protein levels in the ipsilateral spinal dorsal horn. *Pain* 137:532-539.
Miyabe T, Miletic G, Miletic V (2006), Loose ligation of the sciatic nerve in rats elicits transient up-regulation of Homer1a gene expression in the spinal dorsal horn. *Neurosci Lett* 398:296-299.
Pulipparacharuvil S, Renthal W, Hale CF, Taniguchi M, Xiao G, Kumar A, Russo SJ, Sikder D, Dewey CM, Davis MM, Greengard P, Nairn AC, Nestler EJ, Cowan CW (2008), Cocaine regulates MEF2 to control synaptic and behavioral plasticity. *Neuron* 59:621-633.
Sandkuhler J (2009), Models and mechanisms of hyperalgesia and allodynia. *Prog Brain Res* 89:707-758.
Smith HS (2009), Calcineurin as a nociceptor modulator. *Pain Physician*, 12: E309-E318.
Strack S, Wadzinski BE, Ebner, FF (1996), Localization of the calcium/calmodulin-dependent protein phosphatase, calcineurin, in the hindbrain and spinal cord of the rat. *J Comp Neurol* 375:66-76.
Taylor BK, Brennan TJ (2000), Preemptive analgesia—moving beyond conventional strategies and confusing terminology. *J Pain* 1:77-84.
Wang GP, Huang LQ, Wu HJ, Zhang L, You ZD, Zhao ZX (2009), Calcineurin contributes to spatial memory impairment induced by rapid eye movement sleep deprivation. *NeuroReport* 20:1172-1176.
Yang Y, Fischer QS, Zhang Y, Baumgartel K, Mansuy IM, Daw NW (2005), Reversible blockade of experience-dependent plasticity by calcineurin in mouse visual cortex. *Nature Neurosci* 8:791-796.
Zimmermann M (1983), Ethical guidelines for investigations of experimental pain in conscious animals. *Pain* 16:109-110.

* cited by examiner

*Primary Examiner* — Susan Hanley
*Assistant Examiner* — Teresa E Knight
(74) *Attorney, Agent, or Firm* — Joseph T. Leone, Esq.; Daniel A. Blasiole; DeWitt, Ross & Stevens, S.C.

(57) ABSTRACT

A method and corresponding pharmaceutical composition to inhibit neuropathic pain by injecting intrathecally into a mammalian subject a neuropathic pain-inhibiting amount of a phosphatase falling within E.C. 3.1.3.x, more specifically a protein phosphatase falling within E.C. 3.1.3.16, and most specifically calcineurin.

15 Claims, 5 Drawing Sheets

METHOD TO INHIBIT NEUROPATHIC PAIN BY INTRATHECAL INJECTION OF PROTEIN PHOSPHATASES

CROSS-REFERENCE TO RELATED APPLICATIONS

Priority is hereby claimed to provisional application Ser. No. 61/498,796, filed Jun. 20, 2011, which is incorporated herein.

FEDERAL FUNDING STATEMENT

This invention was made with government support under NS034870 and NS055042 awarded by the National Institutes of Health. The government has certain rights in this invention.

FIELD OF THE INVENTION

Described herein is a method to treat neuropathic pain by intrathecal injection of phosphatases in general, protein phosphatases in particular, and calcineurin most preferably.

BACKGROUND

Neuropathic pain is caused by damage or disease affecting the somatosensory system. It is often associated with abnormal sensations referred to as dysesthesia. These sensations are perceived by the subject as an unpleasant, abnormal sense of touch, or other sensations such as burning, wetness, itching, electric shock, and pins and needles. Neuropathic pain may also involve pain produced by normally non-painful stimuli (allodynia). Neuropathic pain may chronic and continuous and/or episodic. For example "phantom pain" from an amputated limb or from a part of the body from which the brain no longer receives signals is a type of neuropathic pain. The etiology of neuropathic pain is quite broad, and can be caused by traumatic injuries, spinal cord injury, multiple sclerosis, stroke, diabetes and other metabolic conditions, herpes zoster infection, HIV-related neuropathies, nutritional deficiencies, toxins, remote manifestations of malignancies, immune-mediated disorders and physical trauma to a nerve trunk.

Neuropathic pain is very difficult to treat. At present there is no effective treatment. Only about 40-60% of patients achieve partial relief via conventional therapies. See, for example, Dworkin R H, O'Connor A B, Backonja M, et al. (2007). "Pharmacologic management of neuropathic pain: evidence-based recommendations," Pain 132 (3): 237-51. Thus there remains a long-felt and unmet need for an effective method to treat neuropathic pain.

SUMMARY

Disclosed and claimed herein is a method to inhibit neuropathic pain. The method comprises injecting intrathecally into a mammalian subject a neuropathic pain-inhibiting amount of a phosphatase falling within E.C. 3.1.3.x, wherein x is an integer from 1 to 86. The subject may be a human being. The method also comprises injecting intrathecally into the mammalian subject a neuropathic pain-inhibiting amount of a protein phosphatase falling within E.C. 3.1.3.16. Again, the subject may be a human being. The method also comprising injecting intrathecally into the mammalian subject a neuropathic pain-inhibiting amount of calcineurin. Again, the subject may be a human being. The method may optionally comprise intrathecally injecting the phosphatase, protein phasphatase, or calcineurin in combination with a pharmaceutical delivery vehicle suitable for intrathecal injection. In a preferred version, the method comprises injecting intrathecally into the subject a dosage of about 0.2 µg to about 200 µg/kg body weight/day of the phosphatase, protein phosphatase, or calcineurin, administered in a single dose or in multiple doses.

Also disclosed herein is a pharmaceutical composition comprising a neuropathic pain-inhibiting amount of a phosphatase falling within E.C. 3.1.3.x, wherein x is an integer from 1 to 86, in combination with a pharmaceutical delivery vehicle suitable for intrathecal injection. In one version of the composition, the phosphatase contained within the composition is a protein phosphatase falling within E.C. 3.1.3.16. The most preferred phosphatase is calcineurin. The pharmaceutical composition may be in unit dosage form. The unit dosage may contain from about 10 µg to about 1 g of the phosphatase. The unit dosage may contain from about 15 µg to about 15 mg of the phosphatase. Dosages above and below these stated ranges are explicitly within the scope of this disclosure. The phosphatase within the pharmaceutical composition may be protein phosphatase falling within E.C. 3.1.3.16, including calcineurin. The unit dosage may contain from about 10 µg to about 1 g of the calcineurin. The unit dosage may contain from about 15 µg to about 15 mg of the calcineurin.

DETAILED DESCRIPTION

Phosphatases/Protein Phosphatases:

Calcineurin (a protein phosphatase 3) plays a pivotal role in regulating activity-dependent synaptic plasticity in the brain. The present inventors have now found that phosphatases in general, protein phosphatases more specifically, and calcineurin most notably play a pivotal role in regulating the development and maintenance of neuropathic pain. As used herein, "phosphatase" generally refers to any enzyme falling within the EC 3.1.3.x (where x is an integer from 1 to 86, i.e., phosphoric monoester hydrolases). These enzymes include those falling within the following enzyme classification numbers:

EC 3.1.3.1 alkaline phosphatase
EC 3.1.3.2 acid phosphatase
EC 3.1.3.3 phosphoserine phosphatase
EC 3.1.3.4 phosphatidate phosphatase
EC 3.1.3.5 5'-nucleotidase
EC 3.1.3.6 3'-nucleotidase
EC 3.1.3.7 3'(2'),5'-bisphosphate nucleotidase
EC 3.1.3.8 3-phytase
EC 3.1.3.9 glucose-6-phosphatase
EC 3.1.3.10 glucose-1-phosphatase
EC 3.1.3.11 fructose-bisphosphatase
EC 3.1.3.12 trehalose-phosphatase
EC 3.1.3.13 bisphosphoglycerate phosphatase
EC 3.1.3.14 methylphosphothioglycerate phosphatase
EC 3.1.3.15 histidinol-phosphatase
EC 3.1.3.16 phosphoprotein phosphatase
EC 3.1.3.17 [phosphorylase]phosphatase
EC 3.1.3.18 phosphoglycolate phosphatase
EC 3.1.3.19 glycerol-2-phosphatase
EC 3.1.3.20 phosphoglycerate phosphatase
EC 3.1.3.21 glycerol-1-phosphatase
EC 3.1.3.22 mannitol-1-phosphatase
EC 3.1.3.23 sugar-phosphatase
EC 3.1.3.24 sucrose-phosphate phosphatase
EC 3.1.3.25 inositol-phosphate phosphatase
EC 3.1.3.26 4-phytase
EC 3.1.3.27 phosphatidylglycerophosphatase
EC 3.1.3.28 ADP-phosphoglycerate phosphatase
EC 3.1.3.29 N-acylneuraminate-9-phosphatase
EC 3.1.3.30 Now included with EC 3.1.3.31
EC 3.1.3.31 nucleotidase
EC 3.1.3.32 polynucleotide 3'-phosphatase
EC 3.1.3.33 polynucleotide 5'-phosphatase
EC 3.1.3.34 deoxynucleotide 3'-phosphatase
EC 3.1.3.35 thymidylate 5'-phosphatase
EC 3.1.3.36 phosphoinositide 5-phosphatase
EC 3.1.3.37 sedoheptulose-bisphosphatase
EC 3.1.3.38 3-phosphoglycerate phosphatase
EC 3.1.3.39 streptomycin-6-phosphatase
EC 3.1.3.40 guanidinodeoxy-scyllo-inositol-4-phosphatase
EC 3.1.3.41 4-nitrophenylphosphatase
EC 3.1.3.42 [glycogen-synthase-D]phosphatase
EC 3.1.3.43 [pyruvate dehydrogenase (acetyl-transferring)]-phosphatase
EC 3.1.3.44 [acetyl-CoA carboxylase]-phosphatase
EC 3.1.3.45 3-deoxy-manno-octulosonate-8-phosphatase
EC 3.1.3.46 fructose-2,6-bisphosphate 2-phosphatase
EC 3.1.3.47 [hydroxymethylglutaryl-CoA reductase (NADPH)]-phosphatase
EC 3.1.3.48 protein-tyrosine-phosphatase
EC 3.1.3.49 [pyruvate kinase]-phosphatase
EC 3.1.3.50 sorbitol-6-phosphatase
EC 3.1.3.51 dolichyl-phosphatase
EC 3.1.3.52 [3-methyl-2-oxobutanoate dehydrogenase (2-methylpropanoyl-transferring)]-phosphatase
EC 3.1.3.53 [myosin-light-chain]phosphatase
EC 3.1.3.54 fructose-2,6-bisphosphate 6-phosphatase
EC 3.1.3.55 caldesmon-phosphatase
EC 3.1.3.56 inositol-polyphosphate 5-phosphatase
EC 3.1.3.57 inositol-1,4-bisphosphate 1-phosphatase
EC 3.1.3.58 sugar-terminal-phosphatase
EC 3.1.3.59 alkylacetylglycerophosphatase
EC 3.1.3.60 phosphoenolpyruvate phosphatase
EC 3.1.3.61 deleted
EC 3.1.3.62 multiple inositol-polyphosphate phosphatase
EC 3.1.3.63 2-carboxy-D-arabinitol-1-phosphatase
EC 3.1.3.64 phosphatidylinositol-3-phosphatase
EC 3.1.3.65 Now EC 3.1.3.64
EC 3.1.3.66 phosphatidylinositol-3,4-bisphosphate 4-phosphatase
EC 3.1.3.67 phosphatidylinositol-3,4,5-trisphosphate 3-phosphatase
EC 3.1.3.68 2-deoxyglucose-6-phosphatase
EC 3.1.3.69 glucosylglycerol 3-phosphatase
EC 3.1.3.70 mannosyl-3-phosphoglycerate phosphatase
EC 3.1.3.71 2-phosphosulfolactate phosphatase
EC 3.1.3.72 5-phytase
EC 3.1.3.73 adenosylcobalamin/α-ribazole phosphatase
EC 3.1.3.74 pyridoxal phosphatase
EC 3.1.3.75 phosphoethanolamine/phosphocholine phosphatase
EC 3.1.3.76 lipid-phosphate phosphatase
EC 3.1.3.77 acireductone synthase
EC 3.1.3.78 phosphatidylinositol-4,5-bisphosphate 4-phosphatase
EC 3.1.3.79 mannosylfructose-phosphate phosphatase
EC 3.1.3.80 2,3-bisphosphoglycerate 3-phosphatase
EC 3.1.3.81 diacylglycerol diphosphate phosphatase
EC 3.1.3.82 D-glycero-β-D-manno-heptose 1,7-bisphosphate 7-phosphatase
EC 3.1.3.83 D-glycero-α-D-manno-heptose-1,7-bisphosphate 7-phosphatase
EC 3.1.3.84 ADP-ribose 1"-phosphate phosphatase EC 3.1.3.85 glucosyl-3-phosphoglycerate phosphatase
EC 3.1.3.86 phosphatidylinositol-3,4,5-trisphosphate 5-phosphatase Preferred phosphatases are those falling within E.C. 3.1.3.16. Synonyms for this specific class of enzyme include protein phosphatase, phosphoprotein phosphatase, and phosphoprotein phosphohydrolase. The term "protein phosphatase" shall be used herein. As used herein, the phrase "protein phosphatase" encompasses any enzyme that catalyzes the reaction: phospho-protein+$H_2O$→a protein+phosphate. Thus, the term "protein phosphatase" as used herein, includes, but is not limited to protein phosphatase I, protein phosphatase IB, protein phosphatase II, protein phosphatase III, protein phosphatase IV, protein phosphatase 2A, protein phosphatase 2B, protein phosphatase-2C, protein phosphatase C-II, protein phosphatase H-II, protein phosphatase SP, protein D phosphatase, protein phosphatase, phosphopyruvate dehydrogenase phosphatase, phosphospectrin phosphatase, polycation modulated (PCM-) phosphatase, 3-hydroxy 3-methylglutaryl coenzymeA reductase phosphatase, Aspergillus awamori acid protein phosphatase, BCKDH phosphatase, branched-chain alpha-keto acid dehydrogenase phosphatase, calcineurin, casein phosphatase, and HMG-CoA reductase phosphatase.

Calcineurin is a protein phosphatase within E.C. 3.1.3.16, also known as protein phosphatase 3, PPP3CA, and calcium-dependent serine-threonine phosphatase, and formerly known as protein phosphatase 2B (PP2B). It activates the T cells of the immune system and can be blocked by various inhibiting drugs, including the immune system suppressants cyclosporine, pimecrolimus, and tacrolimus.

Thus, described herein is a method to inhibit neuropathic pain comprising injecting intrathecally into a subject a neuropathic pain-inhibiting amount of a protein phosphatase, more preferably a protein phosphatase 3 and most preferably calcineurin.

While not being bound to any underlying mechanism or pathway, nerve injury may give rise to neuropathic pain at least in part as a result of the loss of calcineurin-mediated dephosphorylation in the DH. With no dephosphorylation to prevent a remodeling of the PSD which favors synaptic enhancement, only exaggerated evoked responses would be elicited by primary afferent activity. This enhanced sensory input manifests then as neuropathic pain.

Pharmaceutical Compositions:

Included herein are pharmaceutical compositions comprising one or more protein phosphatases or a pharmaceutically acceptable salt thereof together with a pharmaceutically acceptable carrier therefor and, optionally, other therapeutically active substances in addition to the protein phosphatase or salt thereof. The pharmaceutical compositions comprise an amount of one or more protein phosphatases or a pharmaceutically acceptable salt thereof that is effective to treat neuropathic pain in a mammal suffering therefrom, to which the composition is administered. In a pharmaceutical composition of the invention, the carrier must be pharmaceutically acceptable in the sense of being compatible with other ingredients in the particular composition and not deleterious to the recipient thereof. The compositions include those suitable for parenteral administration in general (including subcutaneous, intramuscular, intradermal, intravenous, and intrathecal) and intrathecal administration in particular.

A "pharmaceutically suitable salt" or "pharmaceutically acceptable salt" (the two phrases are synonymous) is any acid or base addition salt whose counter-ions are non toxic to the patient in pharmaceutical doses of the salts, so that the beneficial effects inherent in the free base or free acid are not vitiated by side-effects ascribable to the counter-ions. A host of pharmaceutically suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis b hydroxynaphthoates, gentisates, isethionates, di p toluoyltartrates, methane sulphonates, ethanesulphonates, benzenesulphonates, p toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like. Other suitable salts are found in, for example, Handbook of Pharmaceutical Salts, P. H. Stahl and C. G. Wermuch, Eds., © 2002, Verlag Helvitica Chemica Acta (Zurich, Switzerland) and S. M. Berge, et al., "Pharmaceutical Salts," *J. Pharm. Sci.*, 66: p. 1-19 (January 1977), both of which are incorporated herein by reference.

In a particular aspect, the pharmaceutical compositions comprise the active ingredient (one or more protein phosphatases or a pharmaceutically acceptable salt thereof) presented in unit dosage form. The term "unit dosage" or "unit dose" is denoted to mean a predetermined amount of the active ingredient sufficient to be effective to treat neuropathic pain. Preferred unit dosage formulations are those containing a daily dose, daily sub-dose, or an appropriate fraction thereof, of the administered active ingredient.

The pharmaceutical compositions may be prepared by any of the methods well known in the art of pharmacy. All methods include the step of bringing the active ingredient into association with a carrier which constitutes one or more accessory ingredients. In general, the compositions are prepared by uniformly and intimately bringing the active ingredient into association with a liquid or solid carrier and then, if necessary, shaping the product into the desired unit dosage form. Clearly, for intrathecal injection, the protein phosphatase is formulated into a suitable liquid form.

Thus, pharmaceutical compositions suitable for parenteral administration, including intrathecal injection, conveniently comprise a sterile injectable preparation of the active ingredient in, for example, a solution which is preferably isotonic with the blood or cerebrospinal fluid of the recipient. Useful formulations also comprise concentrated solutions or solids containing the active ingredient which upon dilution with an appropriate solvent give a solution suitable for parenteral (including intrathecal) administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

In addition to the aforementioned ingredients, the compositions of this invention may further include one or more optional accessory ingredients(s) utilized in the art of pharmaceutical formulations, e.g., diluents, buffers, colorants, binders, surfactants, thickeners, lubricants, suspending agents, preservatives (including antioxidants) and the like.

The amount of active ingredient required to be effective for alleviating neuropathic pain will, of course, vary with the individual mammal being treated and is ultimately at the discretion of the medical or veterinary practitioner. The factors to be considered include the species and sex of the mammal, the condition being treated, the route of administration, the nature of the formulation, the mammal's body weight, surface area, age and general condition, and the particular protein phosphatase(s) to be administered.

In general, the pharmaceutical compositions of this invention contain from about 10 µg to about 1 g and, preferably, from about 15 µg to about 15 mg of the active ingredient, preferably in a unit dosage form. However, a suitable effective dose is in the range of about 0.2 µg to about 200 µg/kg body weight/day, preferably in the range of about 0.2 µg to about 100 µg/kg body weight/day, or about 0.2 µg to 10 µg/kg body weight/day or about 0.2 µg/kg body weight/day to about 5 µg/kg body weight/day calculated as the non-salt form of the phosphatase. The total daily dose may be given as a single dose, multiple doses, e.g., two to six times per day, or by intrathecal infusion for a selected duration. Dosages above or below the range cited above are within the scope of the disclosed method and composition and may be administered to the individual patient if desired and necessary.

For example, for a 75 kg mammal, a dose range would be about 15 µg to about 15 mg per day.

Methods to Treat Neuropathic Pain:

The processing of sensory information in the spinal dorsal horn may change significantly following peripheral nerve injury or inflammation. Ultimately this changed processing may lead to the development of neuropathic pain. For example, a short but intense period of acute injury to the sciatic nerve may lead to persistent pain that far outlasts the initial insult. Much progress has been made in elucidating some of the mechanisms underlying the development of neuropathic pain. Yet many gaps in our knowledge remain and as a result neuropathic pain continues to be inadequately treated. There remains a long-felt and unmet need for a method to alleviate neuropathic pain.

Preliminary studies by the present inventors suggested that the loss of calcium phosphatases in general, and more specifically protein phosphatase 3, also known as calcineurin, at synapses of spinal dorsal horn neurons may lead to the development of neuropathic pain following sciatic nerve injury. As shown in the Examples below, a single intrathecal injection of exogenous calcineurin alleviated well-established neuropathic pain for four days after the injection. This was intriguing and unexpected because a method of effectively relieving or diminishing pain in patients suffering from well-established neuropathic pain is unknown.

Thus, described herein is a method of alleviating, reducing, diminishing or otherwise attenuating neuropathic pain by administering a protein phosphatase intrathecally into a mammal in need of pain relief. The preferred protein phosphatase is calcineurin.

Protein phosphatases in general and calcineurin (protein phosphatase 3, also previously known as protein phosphatase 2B) in particular play a pivotal role in regulating activity-dependent synaptic plasticity in the brain. The development of neuropathic pain appears dependent upon some of the same mechanisms that underlie brain synaptic plasticity. Thus, the inventors hypothesized that protein phosphatases such as calcineurin may similarly play an important role in long-lasting injury-elicited plasticity in the spinal dorsal horn.

Preliminary studies by the present inventors indicated that the loss of calcineurin in the post-synaptic density (PSD) of spinal dorsal horn neurons may lead to the development of neuropathic pain following sciatic nerve injury. The studies (described in the Examples) also demonstrated that a single intrathecal injection of exogenous calcineurin alleviated well-established neuropathic pain for four days after the injection.

While not being limited to any specific underlying mechanism of action, the inventors postulate that the loss of protein phosphatase activity in the PSD critically permits nerve injury-elicited afferent activity to remodel the synapses of spinal dorsal horn neurons in such a way as to allow for the transition to long-lasting plasticity and thus the development of neuropathic pain. In other words, nerve injury may give rise to neuropathic pain at least in part as a result of the loss of protein phosphatase-mediated dephosphorylation in the spinal dorsal horn. With no dephosphorylation to prevent the nerve injury-elicited remodeling of the PSD which favors synaptic enhancement, only exaggerated evoked responses would be elicited by primary afferent activity. This enhanced sensory input manifests then as neuropathic pain.

Treatment of neuropathic pain remains elusive. Several promising drugs have proven ineffective in human clinical trials despite their demonstrated effectiveness in animals. Consequently, the need for novel therapeutic approaches to treat neuropathic pain remains great. These approaches should be based on individualized treatment regimens to maximize analgesic effectiveness. An advantage of protein phosphatase therapy is that protein phosphatases are endogenous substances. Although this does not eliminate all toxic potential, it does reduce the possibility of long-term harm especially when coupled with judicious dosing.

The balance between protein kinase and protein phosphatase activity at the synapse can critically determine overall synaptic strength. As a result, the loss of either one of these activities has the potential to engender long-lasting changes in synaptic function, i.e., long-lasting plasticity. More than a decade ago, Kandel and colleagues described how the interplay between protein kinase A (PKA) and calcineurin was essential in initiating and maintaining long-lasting enhancement of synaptic function in *Aplysia, Drosophila*, mice and rats.

On one hand, activation of PKA by cyclic AMP, and the subsequent phosphorylation of target proteins, resulted in long-term memory storage. On the other hand, activation of calcineurin led to the dephosphorylation of these target proteins to prevent the transition from short to long-term memory. Later studies in other brain areas confirmed the general role of calcineurin in negatively constraining the acquisition of spatial or aversive memory, or of long-lasting plasticity in ocular dominance, cocaine addiction, and vestibular compensation.

It appears that injury-elicited plasticity accompanies peripheral nerve injury and that this significant alteration in sensory processing in the spinal dorsal horn may ultimately contribute to the development of neuropathic pain. Plasticity allows for enhanced neuronal communication. In the brain, it enables learning and memory, but in the spinal dorsal horn it may transform the essential but rapidly terminated sensation of acute pain into unproductive persistent, chronic pain (i.e., neuropathic pain).

The post-synaptic density (PSD) is especially deserving of attention with respect to neuropathic pain because its function may represent a final common reflection of the many injury-elicited changes in receptors, pathways, transcription factors and genes that have been cataloged since the introduction of chronic pain models two decades ago. As detailed in the Examples, the inventors have now shown that the development of chronic pain is a pivotal consequence of the loss of protein phosphatase activity in the PSD of spinal dorsal horn neurons.

Figure 1:
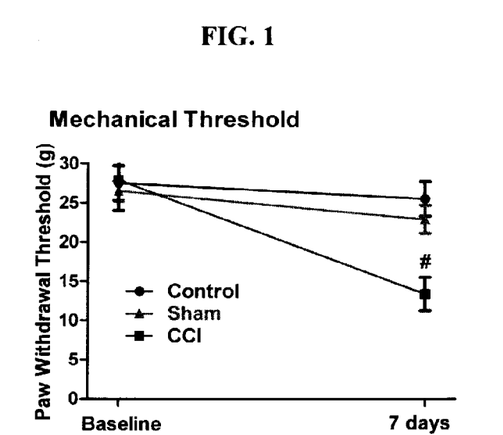
FIG. 1 depicts the mechanical stimulus threshold in control rats (-●-), CCI-altered rats (-■-) and sham-operated rats (-▲-)#=p<0.005. See the examples for full experimental details.
Figure 2:
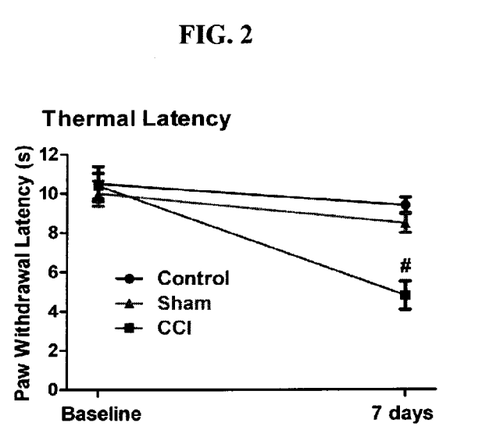
FIG. 2 depicts the thermal latency threshold in control rats (-●-), CCI-altered rats (-■-) and sham-operated rats (-▲-) #=p<0.005. See the examples for full experimental details.
Figure 3:
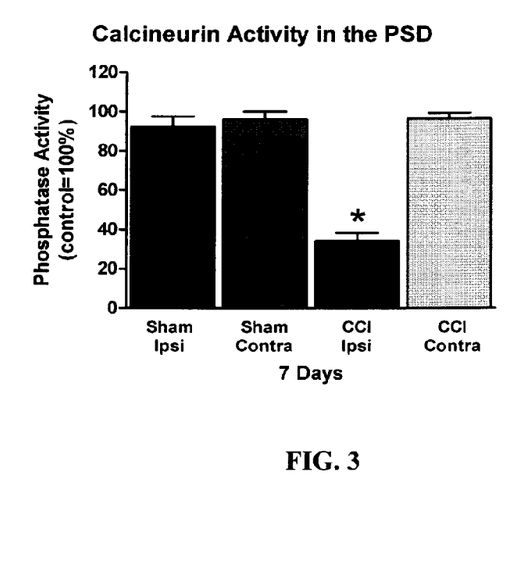
FIG. 3 is a histogram depicting calcineurin activity in the PSD of control, sham-operated, and CCI-altered rats.
Figure 7:
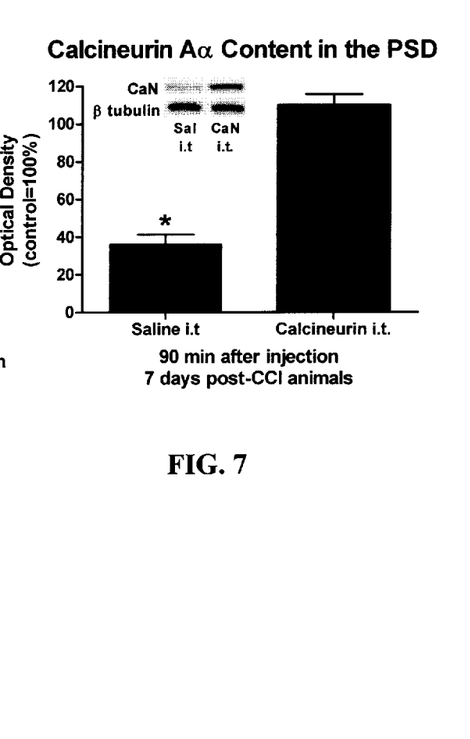
FIG. 7 is a histogram depicting calcineurin Aα isoform content in the post-synaptic density of rats 90 minutes after intrathecal injection of either saline or a single dose of calcineurin. The inset shows the gel from which the histogram was generated.

The data gathered by the inventors (see Examples) confirmed an association between calcineurin and neuropathic pain. There was significantly lower calcineurin activity and content in the ipsilateral PSD of spinal dorsal horn neurons in CCI animals exhibiting neuropathic pain. The pain behavior was attenuated by an intrathecal injection of exogenous calcineurin which accumulated in the PSD. (See FIGS. 1 and 2). The analgesic action of calcineurin was long-lasting as a single intrathecal injection provided pain relief for four days. An intrathecal application of the calcineurin inhibitor FK-506 elicited pain behavior in control, uninjured animals. The same injection significantly reduced calcineurin activity in the PSD. (See FIGS. 7, 8, and 9). For all figures error bars represent the SEM.

EXAMPLES

The following examples are included solely to provide a more complete description of the invention disclosed and claimed herein. The examples do not limit the scope of the invention in any fashion.

Summary of Testing Protocol:

Perform behavioral tests (mechanical thresholds, thermal latencies).

Anesthetize animal. Perform chronic constriction injury (CCI) surgery on sciatic nerve.

Recover the animal and return to animal quarters.

Re-test the behavior seven (7) days-post surgery.

Anesthetize the animal.

Perform intrathecal injection of protein phosphatase (calcineurin was used in the examples).

Recover the animal and return to animal quarters.

Re-test behavior 2, 4 and 6 days after intrathecal calcineurin injection.

Animals:

Male Sprague-Dawley rats (200-250 g, Harlan Laboratories, Madison, Wis.) were used as experimental animals. Water and food was provided ad libitum. All experiments were conducted in accordance with guidelines accepted by the International Association for the Study of Pain (Zimmermann, 1983). The animal protocol (M02113) was approved by the Animal Care Committee of the School of Medicine and Public Health at the University of Wisconsin-Madison.

Mechanical Withdrawal Threshold:

An automated instrument was used for assessing touch sensitivity. An animal was placed inside a plastic box on a raised plasticized wire-mesh surface. The animal is free to move within the confines of the box. The animal acclimates to the apparatus, and a touch stimulator unit was then slid under the animal to position a stainless steel filament (0.5 mm diameter) under the plantar surface of a paw. A button press causes the filament to move perpendicularly to the tested paw. The filament exerts an increasing force, starting below the threshold of detection and increases until the animal withdraws the paw. The force applied to the filament that results in paw withdrawal was recorded.

More specifically, a dual channel scale (Incapacitance Meter™, Stoelting, Chicago, Ill.), which separately measures the weight borne by each hind limb, was used for the weight-bearing tests. (See Miletic and Miletic, 2008). The dual-channel scale separately measures the weight the animal distributes to each hind limb. The force exerted by each limb (measured in grams) is averaged over a user-selectable period, thus indicating any tendency for the animal to shift its weight from one limb to the other. While normal rats distribute weight about equally, animals with a unilateral injury will shift the ratio of weight distribution between an injured and non-injured limb. The difference in weight distribution is taken as a measure of the level of discomfort in the injured limb. In other words, the less weight placed on an injured limb, the greater the level of discomfort. The weight distribution of each hind limb was measured over a 1s period, and the measurement repeated 20 times to obtain an averaged left/right ratio. An important advantage of this test is that it allows assessing (at least to some extent) spontaneous pain behavior. The animal stands and makes its natural adjustment to the degree of pain.

Thermal Withdrawal Latency:

Thermal sensitivity is assessed using the hindpaw withdrawal test to a thermal noxious stimulus. An animal was placed inside a plastic box on a raised glass surface. The animal is free to move within the confines of the box. A movable, focused beam of radiant heat was placed under the glass on which the animal is resting a paw. The glass is progressively heated until a noxious threshold was reached to elicit paw withdrawal. As soon as the animal moved its paw, a photocell in the metal enclosure containing the heat source turned off the light. The latency (in sec) for the animal to withdraw its paw was recorded by a digital automatic display.

For both behaviors, the ipsilateral, injured, paw was tested four times to obtain an average value. Each test is separated by 5 min. Persons performing behavioral tests are blinded to treatment whenever possible.

Anesthesia:

Animals were anesthetized with isoflurane using an anesthesia machine (4% induction, 2-2.5% maintenance). Body temperature was kept at 37° C. with a homeothermic blanket system. Anesthesia was sufficiently deep to prevent arousal, but light enough to permit spontaneous respiration. Surgical anesthetic depth was determined by the loss of corneal and pedal reflexes.

Chronic Constriction Injury (CCI, Loose Ligation of the Sciatic Nerve):

Animals were anesthetized with isoflurane and prepared for surgery by clipping the hair over the mid-thigh area of the left hind leg, scrubbing the clipped area with povidone iodine and alcohol (repeated three times), and lubricating the eyes with sterile ophthalmic ointment. The sciatic nerve was exposed at mid-thigh level by blunt dissection through the biceps femoris muscles. The nerve was freed of adherent tissue, and four ligatures (4.0 chromic gut) were spaced about 1 mm apart. Care was taken to tie the ligatures so that the nerve trunk is just barely constricted when viewed with a dissecting microscope at 40×. This degree of constriction retards, but does not arrest, circulation through the superficial epineural vasculature. The incision was closed in layers using chromic gut sutures for muscle and silk sutures for skin.

Calcineurin Solution:

A stock solution of calcineurin enzyme at a concentration of 100 units/microliter is commercially available (Enzo Life Sciences, Plymouth Meeting, Pa., Cat. No. BML-SE163-5000). The stock solution was diluted 1:10 with saline (1 part of calcineurin stock solution+9 parts of saline) to make a diluted calcineurin solution of 10 units/microliter. Ten microliters of the diluted calcineurin solution was then injected intrathecally. In other words the dose is 100 units of calcineurin per animal. Animal weights were approximately 200 to 250 g. This equates to a dosage of roughly 3 µg/kg body weight (in the rat).

Intrathecal Injection:

The animals were anesthetized with isoflurane and securely held in the sternal position. A 25 µl Hamilton-brand microsyringe was fitted with a 25-gauge, 1-inch hypodermic needle and the needle inserted between the dorsal aspects of L5 and L6 perpendicular to the vertebral column. This site corresponds to the region where the spinal cord ends and the cauda equina begins and was chosen to reduce the possibility of spinal damage. The needle was advanced until a slight but noticeable movement of the tail or the leg was observed. This indicates that the needle has entered into the intrathecal space. Drugs were injected in a volume of 10 µl and the syringe was held in place for a few seconds before being progressively and slowly withdrawn to avoid drug outflow. The rat then recovers from the anesthesia. Any animal that showed signs of motor impairment or other neurological disorders was immediately euthanized with an intracardiac injection of super-saturated potassium chloride solution (>350 mg/ml) after the animal had been first anesthetized with isoflurane.

Tissue Collection for Biochemical Assays:

Animals were anesthetized with isoflurane and while still deeply anesthetized were euthanized with an intracardiac injection of super-saturated potassium chloride (>350 mg/ml). A laminectomy was used to rapidly (<2 min) expose the lumbar spinal cord at L5. About 1 cm of the cord was excised and placed into a Petri dish containing dry-ice-cold saline or homogenizing buffer. Subsequently, the cord was cut under a dissecting microscope into dorsal and ventral halves, and the dorsal half further divided into ipsilateral and contralateral quadrants. All tissues were immediately placed into dry-ice cooled collecting tubes, and stored at −80° C. until used.

Tissue Collection for Double Immunofluorescence:

Animals were first rendered unconscious with isoflurane and then deeply anesthetized with sodium pentobarbital (60 mg/kg). Subsequently, the animals were injected intracardially with 0.5 ml heparin (1000 iu/ml), and perfused intracardially with 4% paraformaldehyde in 0.2M phosphate buffered-saline (PBS). The fixed lumbar spinal cord (~L5) was removed and cryoprotected in 30% sucrose and 5% glycerin in 0.1M PBS, and stored for a few days before sectioning.

RT-PCR, Enzyme Activity Assay and Immunoblots:

Calcineurin mRNA levels were determined by monitoring in real-time the increase in fluorescence of SYBR-GREEN dye with the ABI Prism 7300 Sequence Detection System (Applied Biosystems, Foster City, Calif.) as detailed previously (Miyabe et al., 2006). Relative expression levels of calcineurin in each sample were determined using a standard curve of 3-fold serial dilutions. Average fold induction relative to control animals was determined after normalizing to the amount of 18S rRNA in each sample. A 2-fold or greater change was considered significant. Primer sequences not shown.

Calcineurin activity was obtained with a commercial kit (Enzo Life Sciences, Plymouth Meeting, Pa.) and expressed as nmol of phosphate released/min/mg of protein. Immunoblots were performed as described previously (Miletic et al., 2002). Calcineurin isoform Aα (Millipore, Billerica, Mass.) was used at a dilution of 1:1000. Developed membranes were stripped and re-probed with beta III tubulin (1:1000; Promega, Madison, Wis.) as the loading control. Protein levels were estimated with the BioSpectrum 500 Image Analysis System (UVP, Upland, Calif.). The calcineurin Aα content within a gel was expressed over the beta III tubulin content, and then the content in sham-operated or CCI animals was normalized to those in control animals. The same normalization procedure was used for the enzyme activity assay.

Statistical Analysis:

ANOVA was used for the statistical data analysis. The main emphasis was on detecting differences in behavior, calcineurin message, activity, or protein content between control, sham-operated and CCI animals, or vehicle and drug-treated animals. Significant effects were further analyzed with Scheffe's post-hoc test. Statistical difference was inferred at $p<0.05$. All data are expressed as mean±SEM.

Figure 4:
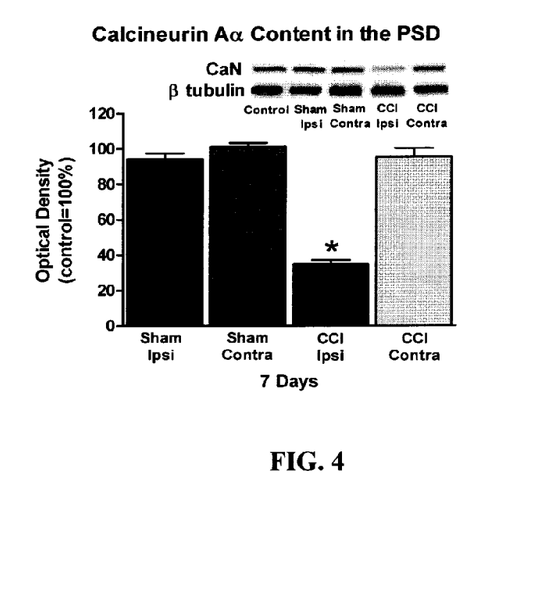
FIG. 4 is a histogram depicting calcineurin Aα isoform content in the PSD of control, sham-operated, and CCI-altered rats.

Lower Calcineurin Activity and Content in PSD of Spinal Dorsal Horn Neurons in CCI Animals Exhibiting Neuropathic Pain:

There was significantly lower calcineurin activity and calcineurin content in the ipsilateral PSD of spinal dorsal horn neurons in CCI animals exhibiting neuropathic pain. See FIGS. 1, 2, 3, and 4. As shown in these four figures, loss of calcineurin activity and protein content in the PSD of spinal dorsal horn neurons was associated with pain behavior. Here, CCI animals were tested for mechanical threshold (FIG. 1) and thermal threshold (FIG. 2) and then assayed for calcineurin activity (FIG. 3) and calcineurin content in the PSD of spinal dorsal horn neurons (FIG. 4). Mechanical and thermal hypersensitivity was observed seven (7) days post-CCI (FIGS. 1 and 2, respectively) and were accompanied by a significant loss of calcineurin activity (FIG. 3) and content of the Aα isoform (~60 kDa) in the ipsilateral PSD (FIG. 4). In contrast, calcineurin activity or content in the contralateral PSD of CCI animals or either side in sham-operated animals was not different from controls. See FIGS. 3 and 4, respectively. Neither control uninjured nor sham-operated animals exhibited pain behavior. For each group n=3. In FIGS. 1, 2, 3, and 4, CaN=calcineurin. $^\#p<0.005$, $*p<0.001$.

Figure 5:
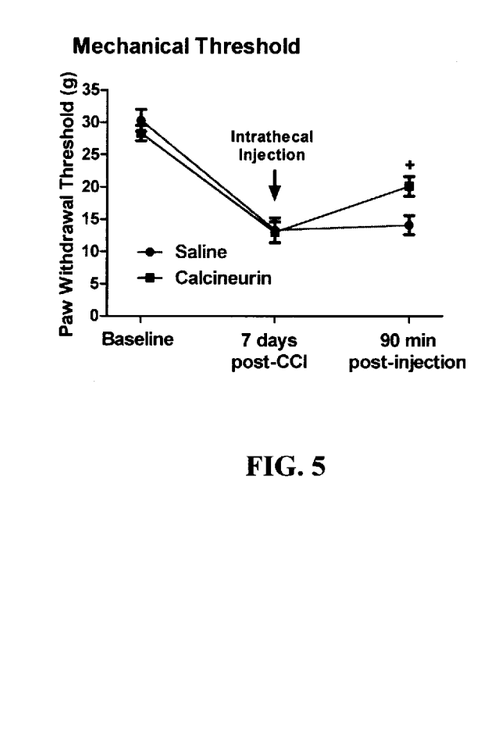
FIG. 5 depicts the mechanical stimulus threshold in CCI-altered rats subject to a single intrathecal injection of calcineurin (-■-) or saline (-●-). +=p<0.01 when compared to pre-injection behavior. See the examples for full experimental details.
Figure 6:
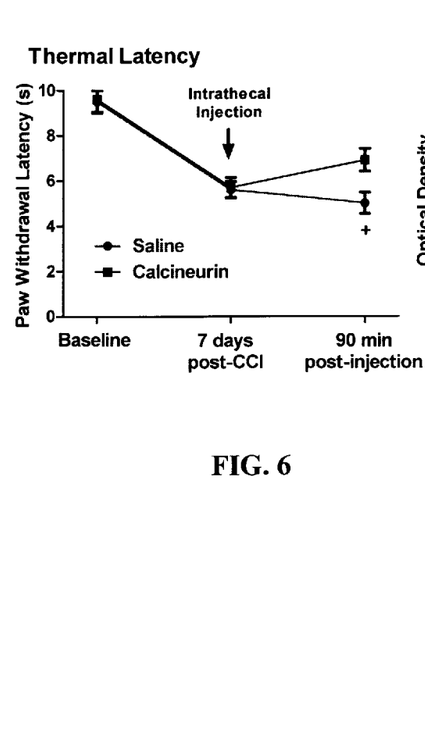
FIG. 6 depicts the thermal latency threshold in CCI-altered rats subject to a single intrathecal injection of calcineurin (-■-) or saline (-●-). +=p<0.01 when compared to pre-injection behavior. See the examples for full experimental details.

Intrathecal Injection of Exogenous Calcineurin Alleviated Mechanical and Thermal Hypersensitivity Following CCI:

Here, animals were subjected to the CCI surgery and tested for pain behavior. CCI animals exhibited typical pain behavior 7 days post-ligation. See FIGS. 5 and 6. Saline (n=3) or calcineurin (100 unit total dose in 10 µl vehicle) (n=3) were then injected intrathecally and the animals were behaviorally retested 90 min after the injection. Both the mechanical and the thermal hypersensitivity were significantly attenuated in the calcineurin injected animals. Again, see FIGS. 5 and 6. In these same animals there was significantly more calcineurin Aα in their ipsilateral PSD. See FIG. 7; $^+p<0.01$ when compared to the pre-injection behavior; $*p<0.001$ vs. control.

This example shows that adding exogenous phosphatase enzyme by intrathecal injection alleviates pain behavior. This may be a result of the phosphatase's accumulation in the PSD.

Duration of Analgesia from a Single Intrathecal Injection of Calcineurin:

To examine the duration of the analgesic action of calcineurin, the behavior of animals with chronic constriction injury (CCI) of the sciatic nerve was tested 2, 4 and 6 days after a single injection of calcineurin (10 units/microliters). The goal of this example was to investigate the longevity of the analgesic action of calcineurin by performing an experiment in chronic constriction injury (CCI) animals and repeatedly testing the behavior two, four and six days after the calcineurin injection.

As expected, the CCI animals exhibited both mechanical and thermal hypersensitivity seven (7) days after the ligation. These animals were then anesthetized and injected intrathecally with saline (n=3) or calcineurin (n=6). Two days later the animals were behaviorally retested. In the calcineurin-treated animals both the mechanical and thermal hypersensitivity were significantly attenuated. See FIGS. 8 and 9, respectively. The calcineurin-treated CCI animals continued to exhibit analgesia when they were behaviorally retested four (4) days after the intrathecal injection. It was only six (6) days after the injection that the calcineurin-treated CCI animals exhibited once again mechanical and thermal hypersensitivity suggesting that calcineurin analgesia had ended. Saline-treated CCI animals exhibited typical pain behavior throughout the testing period. See FIG. 10 (mechanical threshold in the control animals) and FIG. 11 (thermal latency in the control animals).

These data establish that a single intrathecal injection of calcineurin provides continual pain relief for at least four (4) days.

Figure 8:
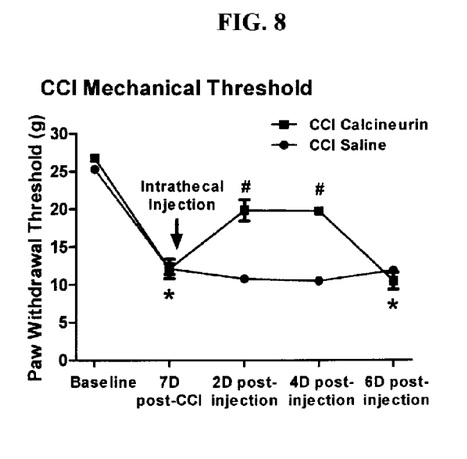
FIG. 8 depicts the mechanical stimulus threshold in CCI-altered rats subjected to a single intrathecal injection of calcineurin (-■-) and control CCI-altered rats subjected to an injection of saline (-●-). *Significantly different from baseline. #Significantly different from the pre-injection behavior. See the examples for full experimental details.
Figure 9:
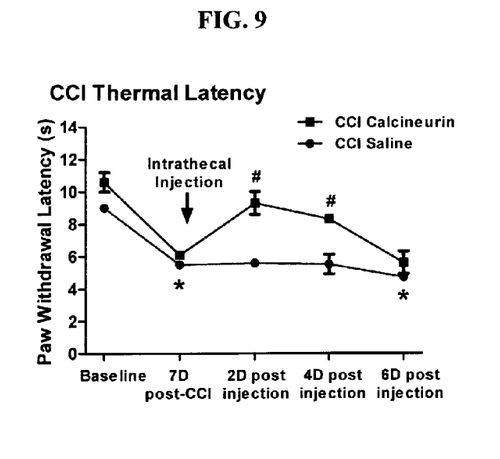
FIG. 9 depicts the thermal latency threshold in CCI-altered rats subjected to a single intrathecal injection of calcineurin (-■-) and control CCI-altered rats subjected to an injection of saline (-●-). *Significantly different from baseline. #Significantly different from the pre-injection behavior.

As shown in FIGS. 8 and 9, the CCI animals exhibited both mechanical hypersensitivity (FIG. 8, -●-) and thermal hypersensitivity (FIG. 9, -●-) as signs of pain behavior seven days post-CCI. These animals were then anesthetized and injected intrathecally with calcineurin (n=4) or saline vehicle (n=3). In the calcineurin-treated animals both the mechanical hypersensitivity (FIG. 8, -■-) and thermal hypersensitivity (FIG. 9, -■-) were attenuated two (2) and four (4) days after the injection. It was only six (6) days after the injection that the calcineurin-treated animals exhibited pain behavior suggesting that the calcineurin analgesia had ended. Vehicle-treated CCI animals exhibited typical pain behavior which persisted throughout the testing period. See FIGS. 8 and 9, -●-.

Figure 10:
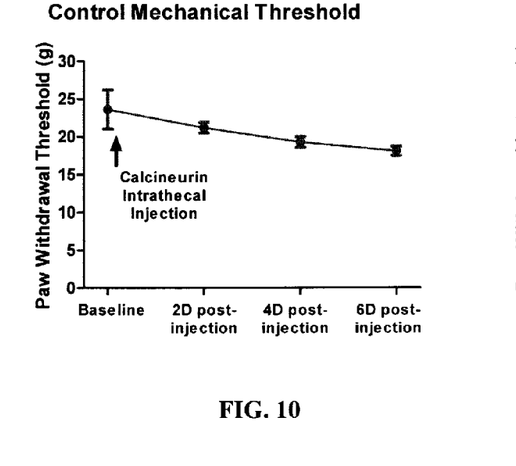
FIG. 10 depicts the mechanical stimulus threshold in unaltered rats subjected to a single intrathecal injection of calcineurin.
Figure 11:
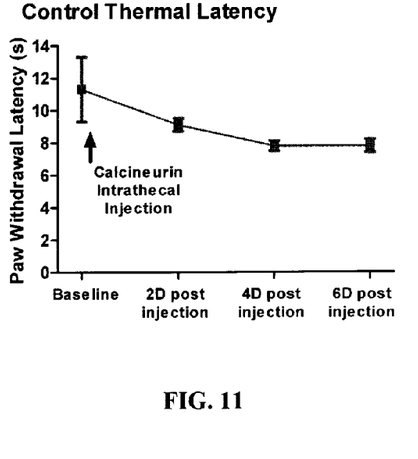
FIG. 11 depicts the thermal latency threshold in unaltered rats subjected to a single intrathecal injection of calcineurin.

The behavior of three control, uninjured, animals was not modified by the intrathecal injection of calcineurin. FIG. 10 depicts the results in the control animals for mechanical stimulation; FIG. 11 depicts the results for the control animals for thermal stimulation.

Repeated measures ANOVA confirmed that the difference between the saline treatment and the calcineurin treatment was statistically significant.

Thus, as shown by this example, a single intrathecal application of exogenous calcineurin elicited prolonged analgesia in neuropathic animals. CCI-altered animals exhibited typical pain behavior seven (7) days post-CCI. After the behavioral testing, saline vehicle (10 μl) or calcineurin (100 units in 10 μl) were injected intrathecally and the animals were behaviorally retested 2, 4, and 6 days after the single injection. Both the mechanical and the thermal hypersensitivity were significantly attenuated in the calcineurin injected animals two (2) and four (4) days post-injection. By six (6) days post-injection, the pain behavior returned. Saline-injected animals exhibited pain behavior throughout the repeated testing. These data indicate that a single intrathecal injection of calcineurin provided pain relief for at least four (4) days. Control, uninjured animals did not show pain behavior and were unaffected by the calcineurin injection. See FIGS. 10 and 11. The results depicted in FIGS. 1 and 2 were significantly different from the pre-injection behavior (#$p<0.005$) and also significantly different from the baseline (*$p<0.001$ vs. control).

Biochemistry with Behavior Study:

The goal of this example was to investigate whether the prolonged analgesic action of calcineurin (10 units/μl, 10 μl injection, 100 units total dose) was associated with the restoration of activity or protein content of the enzyme in the postsynaptic density of spinal dorsal horn neurons. The example analyzed data from 18 animals.

Baseline behavior was first established. Then the chronic constriction injury (CCI) surgery was performed the same day. Seven (7) days later behavior was re-tested. The animals were then assigned to individual groups depending on the duration of the post-injection period (i.e., 2, 4, 6 days). After the last behavioral test the animals were euthanized and their lumbar spinal dorsal horn tissues collected for the calcineurin activity and protein content assays. These data are called "group" data to differentiate them from the "continuous" data in which the same animal was tested at 2, 4, and 6 days, post-injection.

Figure 12:
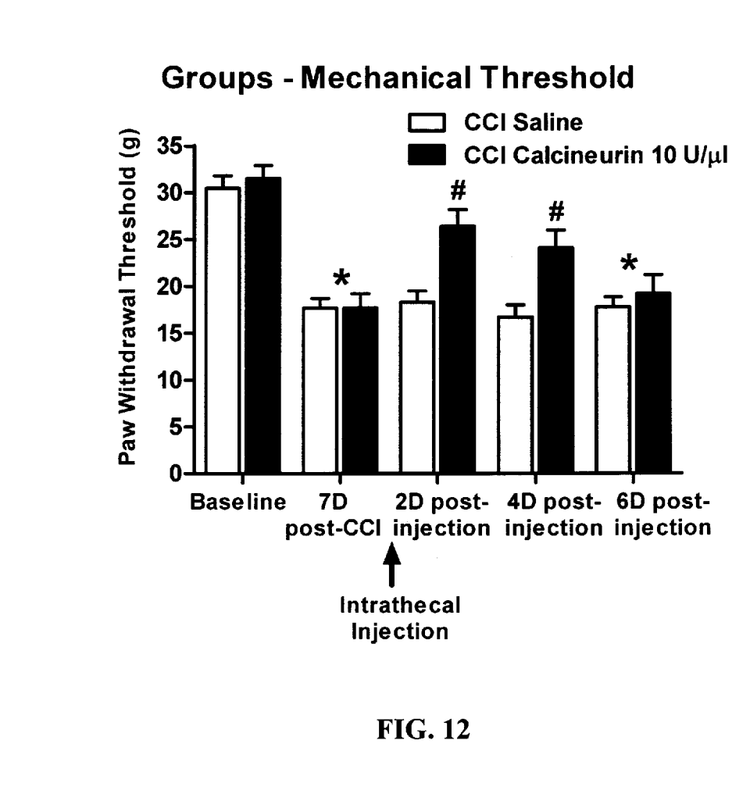
FIG. 12 depicts the mechanical stimulus threshold in CCI-altered rats subjected to a single intrathecal injection of calcineurin and control CCI-altered rats subjected to an injection of saline. *Significantly different from baseline. #Significantly different from the pre-injection behavior. See the examples for full experimental details.
Figure 13:
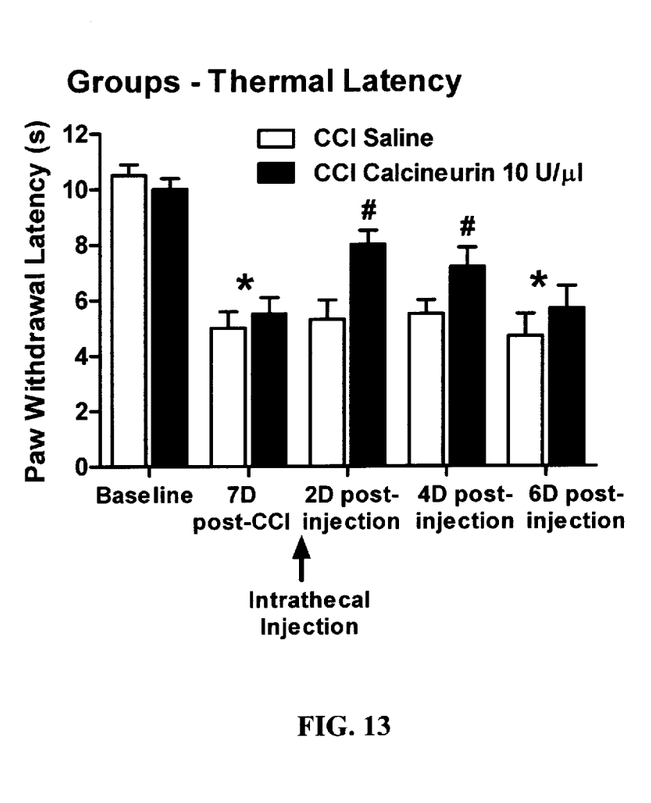
FIG. 13 depicts the thermal latency threshold in CCI-altered rats subjected to a single intrathecal injection of calcineurin and control CCI-altered rats subjected to an injection of saline. *Significantly different from baseline. #Significantly different from the pre-injection behavior.

As can be seen from FIGS. 12 and 13, all of the behavioral results confirmed the data from the continuous calcineurin study depicted in FIGS. 8 and 9. In other words, a single intrathecal injection of calcineurin provided analgesia in both the 2- and 4-day post-injection animal groups. The analgesic effect of calcineurin disappeared in the 6-day post-injection group. Saline-injected CCI animal groups exhibited typical pain behavior at all testing time points.

FIGS. 12 and 13 show that a single intrathecal application of exogenous calcineurin (10 units/microliter, 100 unit total dose) provided prolonged analgesia in neuropathic animals. All 18 CCI animals exhibited typical pain behavior 7 days post-ligation. After the behavioral testing, half of the animals were injected intrathecally with saline (n=9) and the other half with calcineurin (n=9). The individual animal groups were then behaviorally retested 2, 4, or 6 days after the single injection (n=3 in each group). The results depicted in FIGS. 5 and 6 were significant: # $p<0.005$ when compared to the pre-injection behavior; *$p<0.001$ vs. control.

Figure 14:
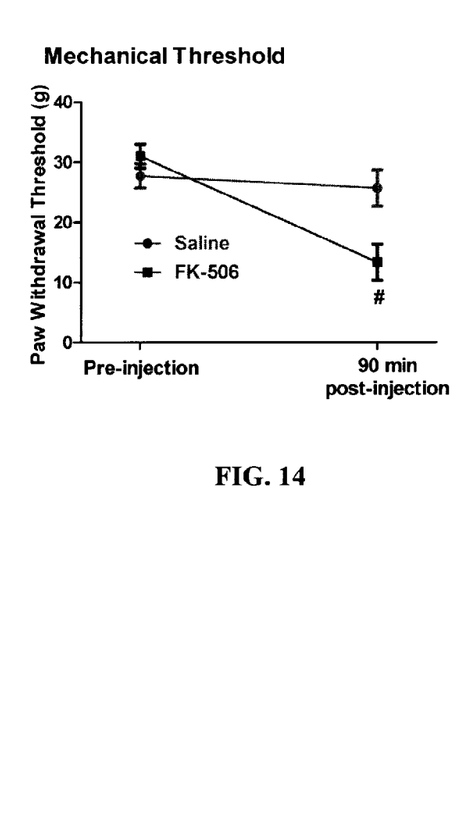
FIG. 14 depicts the mechanical stimulus threshold in control rats injected with saline (-●-) and rats subjected to a single injection of FK-506 (-■-).
Figure 15:
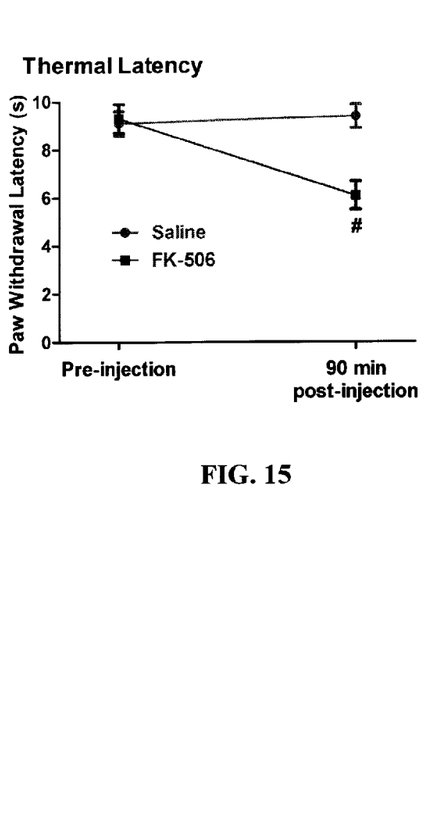
FIG. 15 depicts the thermal latency threshold in control rats injected with saline (-●-) and rats subjected to a single injection of FK-506 (-■-).
Figure 16:
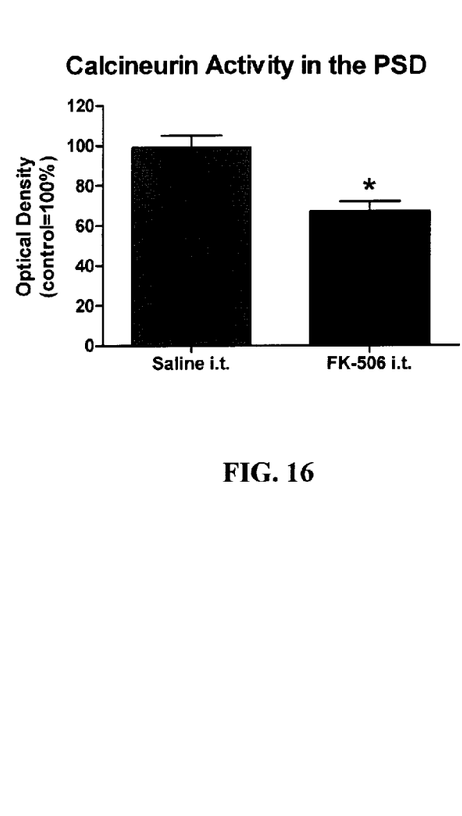
FIG. 16 is a histogram depicting calcineurin activity in the post-synaptic density in saline-injected rates and rats injected with FK-506.

Intrathecal Injection of FK-506 Elicited Mechanical and Thermal Hypersensitivity in Control, Uninjured Animals:

Here, control animals were given an injection of FK-506, a calcineurin inhibitor. Thus, the purpose of this Example was to assess whether the loss of calcineurin activity in the spinal dorsal horn would elicit pain behavior in control, uninjured animals. Ninety (90) minutes after an intrathecal injection of the calcineurin inhibitor FK-506 (n=3) there was a significant decrease in mechanical withdrawal thresholds (FIG. 14) and thermal latencies (FIG. 15) in control, uninjured animals (-■-) as compared to control, uninjured animals injected with saline (-●-). In these same animals there was also a significant decrease in calcineurin activity in their PSD. See FIG. 16; #$p<0.005$, *$p<0.001$.

These data show that inhibition of calcineurin activity in the PSD leads to pain behavior.

REFERENCES

Abel T, Kandel E (1998), Positive and negative regulatory mechanisms that mediate long-term memory storage. Brain Res Rev 26:360-378.

Baumgartel K, Genoux D, Welzl H, Tweedie-Cullen R Y, Koshibu K, Livingstone-Zatchej M, Mamie C, Mansuy I M (2008), Control of the establishment of aversive memory by calcineurin and Zif268. Nature Neurosci 11:572-578.

Bennett G J, Xie Y K (1997), A peripheral mononeuropathy in rat that produces disorders of pain sensation like those seen in man. Pain 33:87-107.

Citri A, Malenka R C (2008), Synaptic plasticity: multiple forms, functions, and mechanisms. Neuropsychopharmacol 33:18-41.

Goto S, Hirano A, Pearson J (1990), Calcineurin and synaptophysin in the human spinal cord of normal individuals and patients with familial dysautonomia. Acta Neuropathol 79:647-652.

Groth R D, Dunbar R L, Mermelstein P G (2004), Calcineurin regulation of neuronal plasticity. Biochem Biophys Res Comm 311:1159-1171.

Groth R D, Coicou L G, Mermelstein P G, Seybold V S (2007), Neurotrophin activation of NFAT-dependent transcription contributes to the regulation of pro-nociceptive genes. J Neurochem 102:1162-1174.

Ji R R, Strichartz, G (2004), Cell signaling and the genesis of neuropathic pain. Science's STKE 252:re14.

Latremoliere A, Woolf C J (2009), Central sensitization: a generator of pain hypersensitivity by central neural plasticity. J Pain 10:895-926.

Lee, H K (2006), Synaptic plasticity and phosphorylation. Pharmacol Therap 112: 810-832.

Masumura C, Horii A, Mitani K, Kitahara T, Uno A, Kubo T (2007), Unilateral vestibular deafferentation-induced changes in calcium signaling-related molecules in the rat vestibular nuclear complex. Brain Res 1138:129-135.

Miletic G, Pankratz M T, Miletic V (2002), Increases in the phosphorylation of cyclic AMP response element binding protein (CREB) and decreases in the content of calcineurin accompany neuropathic pain following chronic constriction injury in rats. Pain 99:493-500.

Miletic G, Miletic V (2008), Loose ligation of the sciatic nerve is associated with TrkB receptor-dependent decreases in KCC2 protein levels in the ipsilateral spinal dorsal horn. Pain 137:532-539.

Miyabe T, Miletic G, Miletic V (2006), Loose ligation of the sciatic nerve in rats elicits transient up-regulation of Homer1a gene expression in the spinal dorsal horn. Neurosci Lett 398:296-299.

Pulipparacharuvil S, Renthal W, Hale C F, Taniguchi M, Xiao G, Kumar A, Russo S J, Sikder D, Dewey C M, Davis M M, Greengard P, Nairn A C, Nestler E J, Cowan C W (2008), Cocaine regulates MEF2 to control synaptic and behavioral plasticity. Neuron 59:621-633.

Sandkuhler J (2009), Models and mechanisms of hyperalgesia and allodynia. Prog Brain Res 89:707-758.

Smith H S (2009), Calcineurin as a nociceptor modulator. Pain Physician, 12: E309-E318.

Strack S, Wadzinski B E, Ebner, F F (1996), Localization of the calcium/calmodulin-dependent protein phosphatase, calcineurin, in the hindbrain and spinal cord of the rat. J Comp Neurol 375:66-76.

Taylor B K, Brennan T J (2000), Preemptive analgesia—moving beyond conventional strategies and confusing terminology. J Pain 1:77-84.

Wang G P, Huang L Q, Wu H J, Zhang L, You Z D, Zhao Z X (2009), Calcineurin contributes to spatial memory impairment induced by rapid eye movement sleep deprivation. NeuroReport 20:1172-1176.

Yang Y, Fischer Q S, Zhang Y, Baumgartel K, Mansuy I M, Daw N W (2005), Reversible blockade of experience-dependent plasticity by calcineurin in mouse visual cortex. Nature Neurosci 8:791-796.

Zimmermann M (1983), Ethical guidelines for investigations of experimental pain in conscious animals. Pain 16:109-110.

What is claimed is:

1. A method to inhibit neuropathic pain comprising injecting intrathecally into a mammalian subject a neuropathic pain-inhibiting amount of a protein phosphatase falling within E.C. 3.1.3.16.

2. The method of claim 1, wherein the subject is a human being.

3. The method of claim 1, comprising intrathecally injecting the phosphatase in combination with a pharmaceutical delivery vehicle suitable for intrathecal injection.

4. The method of claim 3, comprising injecting intrathecally into the subject a dosage of about 0.2 to about 200 µg/kg body weight/day of the phosphatase administered in a single dose or in multiple doses.

5. A method to inhibit neuropathic pain comprising injecting intrathecally into a mammalian subject a neuropathic pain-inhibiting amount of calcineurin.

6. The method of claim 5, wherein the subject is a human being.

7. The method of claim 5, comprising intrathecally injecting the calcineurin in combination with a pharmaceutical delivery vehicle suitable for intrathecal injection.

8. The method of claim 5, comprising injecting intrathecally into the subject a dosage of about 0.2 to about 200 µg/kg body weight/day of the calcineurin administered in a single dose or in multiple doses.

9. A method to inhibit neuropathic pain comprising injecting intrathecally into a mammalian subject a neuropathic pain-inhibiting amount of a phosphatase falling within E.C. 3.1.3.16, wherein the phosphatase is selected from the group consisting of calcineurin, protein phosphatase 1, protein phosphatase 2A, and protein phosphatase 2C.

10. The method of claim 9, wherein the subject is a human being.

11. The method of claim 9, comprising intrathecally injecting the phosphatase in combination with a pharmaceutical delivery vehicle suitable for intrathecal injection.

12. The method of claim 9, comprising injecting intrathecally into the subject a dosage of about 0.2 to about 200 µg/kg body weight/day of the phosphatase administered in a single dose or in multiple doses.

13. The method of claim 9, comprising injecting intrathecally into the mammalian subject a neuropathic pain-inhibiting amount of protein phosphatase 1.

14. The method of claim 9, comprising injecting intrathecally into the mammalian subject a neuropathic pain-inhibiting amount of protein phosphatase 2A.

15. The method of claim 9, comprising injecting intrathecally into the mammalian subject a neuropathic pain-inhibiting amount of protein phosphatase 2C.

* * * * *